United States Patent
Soloway

(10) Patent No.: US 10,004,912 B1
(45) Date of Patent: Jun. 26, 2018

(54) SYSTEM AND METHOD FOR DIAGNOSING AND TREATING CARDIAC ARRHYTHMIA

(71) Applicant: CARDIOSPARK LLC, Tucson, AZ (US)

(72) Inventor: Norman P. Soloway, Tucson, AZ (US)

(73) Assignee: CARDIOSPARK LLC, Tucson, AZ (US)

( * ) Notice: Subject to any disclaimer, the term of this patent is extended or adjusted under 35 U.S.C. 154(b) by 0 days. days.

(21) Appl. No.: 15/661,398

(22) Filed: Jul. 27, 2017

Related U.S. Application Data

(60) Provisional application No. 62/367,547, filed on Jul. 27, 2016, provisional application No. 62/377,160, filed on Aug. 19, 2016.

(51) Int. Cl.
*A61N 1/39* (2006.01)
*A61N 1/04* (2006.01)
*A61B 5/046* (2006.01)
*A61B 5/00* (2006.01)

(52) U.S. Cl.
CPC ............ *A61N 1/3987* (2013.01); *A61B 5/046* (2013.01); *A61B 5/4836* (2013.01); *A61N 1/046* (2013.01); *A61N 1/3904* (2017.08); *A61N 1/3925* (2013.01)

(58) Field of Classification Search
CPC ............ A61N 1/36014; A61N 1/36017; A61N 1/3625; A61N 1/39; A61N 1/3904; A61N 1/046
See application file for complete search history.

(56) References Cited

U.S. PATENT DOCUMENTS

| | | | |
|---|---|---|---|
| 5,645,522 A | 7/1997 | Lurie et al. | 601/43 |
| 7,657,311 B2 | 2/2010 | Bardy et al. | 607/2 |
| 7,672,720 B2 | 3/2010 | Heath | 607/5 |
| 8,050,759 B2 | 11/2011 | Stegemann et al. | 607/17 |
| 8,078,288 B2 | 12/2011 | Heath | 607/142 |
| 8,260,413 B2 | 9/2012 | Heath | 607/5 |
| 8,301,232 B2 | 10/2012 | Albert et al. | 600/509 |
| 8,509,882 B2 | 8/2013 | Albert et al. | 600/509 |
| 8,615,295 B2 | 12/2013 | Savage et al. | 607/5 |
| 8,700,137 B2 | 4/2014 | Albert | 600/513 |
| 8,781,576 B2 | 7/2014 | Savage et al. | 607/5 |
| 9,026,202 B2 | 5/2015 | Albert | A61B 5/0404 |

(Continued)

OTHER PUBLICATIONS

"www.alivecor.com" AliveCor company website for Kardia Mobile, personal EKG. Printed Aug. 9, 2017 (9 pages).

(Continued)

*Primary Examiner* — Allen Porter, Jr.
(74) *Attorney, Agent, or Firm* — Hayes Soloway P.C.

(57) ABSTRACT

Electrically conductive implantable microelectrodes or microconductors are used to lower the transthoracic impedance of an animal. An adapter is provided to enable use of a separate electronic device such as a smartphone or tablet in connection with the implanted microelectrodes or microconductors as an automatic external defibrillator (AED). The adapter includes a connector to connect the adapter to the electronic device, at least one capacitor that may be charged to a predetermined level from the power source of the electronic device, and an electrode through which an electric shock may be delivered from the capacitor through the implanted microelectrodes or microconductors to the heart of the animal.

14 Claims, 2 Drawing Sheets

(56) References Cited

U.S. PATENT DOCUMENTS

| | | | |
|---|---|---|---|
| 9,101,778 B2 | 8/2015 | Savage et al. | A61N 1/3918 |
| 2003/0149423 A1* | 8/2003 | Fischell | A61L 27/54 |
| | | | 604/892.1 |
| 2005/0143776 A1 | 6/2005 | Brown | A61N 1/18 |
| 2006/0173498 A1 | 8/2006 | Banville et al. | A61N 1/39 |
| 2010/0030290 A1* | 2/2010 | Bonner | A61N 1/385 |
| | | | 607/5 |
| 2010/0241181 A1 | 9/2010 | Savage et al. | 607/5 |
| 2014/0005736 A1* | 1/2014 | Geheb | A61N 1/3987 |
| | | | 607/7 |
| 2014/0039593 A1 | 2/2014 | Savage et al. | A61N 1/046 |
| 2014/0039594 A1 | 2/2014 | Savage et al. | A61N 1/046 |
| 2014/0323923 A1 | 10/2014 | Khuon et al. | 600/595 |
| 2014/0324111 A1* | 10/2014 | Wu | A61N 1/3993 |
| | | | 607/7 |
| 2015/0217121 A1 | 8/2015 | Subramanian et al. | A61N 1/39 |
| 2016/0038751 A1 | 2/2016 | Broder et al. | A61N 1/39 |

OTHER PUBLICATIONS

International Preliminary Report on Patentability issued in application No. PCT/US2016/023295, dated Sep. 28, 2017 (7 pgs).

* cited by examiner

SYSTEM AND METHOD FOR DIAGNOSING AND TREATING CARDIAC ARRHYTHMIA

CROSS REFERENCE TO RELATED APPLICATIONS

This application claims priority from U.S. Provisional Application Ser. No. 62/367,547, filed Jul. 27, 2016, and from U.S. Provisional Application Ser. No. 62/377,160, filed Aug. 19, 2016, the contents of which are incorporated herein by reference.

BACKGROUND OF THE INVENTION

Field of the Invention

An automatic external defibrillator (AED) is a portable electronic device that diagnoses life-threatening cardiac arrhythmias of ventricular fibrillation and ventricular tachycardia in a person, and is able to treat them through application of electrical shock which stops the arrhythmia, allowing the heart to reestablish an effective rhythm. Used in connection with EKG data, an AED may diagnose life-threatening cardiac arrhythmias of ventricular fibrillation and ventricular tachycardia in a person, and treat them through application of electrical shock which stops the arrhythmia, allowing the heart to reestablish an effective rhythm.

Description of Related Art

Uncorrected, cardiac conditions rapidly lead to irreversible brain damage and death, once cardiac arrest takes place. After approximately three to five minutes of cardiac arrest, irreversible brain/tissue damage may begin to occur. For every minute that a person in cardiac arrest goes without being successfully treated (by defibrillation), the chance of survival decreases by 7% per minute for the first three minutes and then decreases by 10% per minute beyond the first 3-5 minutes.

AEDs are increasingly being installed in public places. Also, as AEDs prices are beginning to fall, some individuals are purchasing AEDs for their homes.

Current AEDs produce a shock in the range of 120-200 joules or above to overcome the transthoracic impedance of a patient to deliver a therapeutic current of the AED to the patient's heart. It is known that the main impediment in the passage of electrical current through the skin is attributed to the dead keratin layers of the stratum corneum (SC). These layers, which are relatively dry, possess low electrical conductivity and consequently inhibit the electromotive forces of any iontophoretic device, such as an AED. Because of the high impedance of the SC, electrical current has to pass through the deeper layers of the skin, i.e. the lower epidermis and the dermis, thereby, carrying active agents into the deep layers and subsequently, into the systemic circulation. Thus, improving SC conductivity should result in more electrical current passing through the SC and consequently, higher delivery of the active electrical impulse to the target organ, in this case, the myocardium, rather than being attenuated through the external layers of the skin.

Recently one company, CardioThrive has proposed compact AEDs which operate producing a much lower shock of about 22 joules. CardioThrive's devices reportedly use a different wave form and paddles having a plurality of microneedles which permit them to use a significantly lower shock to revive a victim. Generally, conductive protrusions are arranged to press or penetrate into the skin of the victim. Such pressing or penetration reportedly reduces the electrical resistance of the skin (e.g., reduces the patient transthoracic impedance for the purpose of delivering a therapeutic current.) As a result, less voltage needs to be generated at the conductive protrusions to ensure a current sufficient to arrest a cardiac arrhythmia in the victim. However, even with improved paddles and wave forms, impedance remains a problem. Even with these advances, AEDs remain bulky, and are too large to be carried on a person.

A typical protocol for using the AED is as follows. Initially, the person who has suffered from sudden cardiac arrest is placed on the floor and clothing is removed to expose the person's chest. The pads of the AED are applied to appropriate locations on the chest, a reading is taken to determine if the person is in arrhythmia, and, if appropriate, the electrical system within the base unit of the AED charges a capacitor to generate a high voltage between the two pads, which delivers an electrical shock to the person. Ideally, the shock restores a normal cardiac rhythm, though in some cases, multiple shocks are required.

SUMMARY OF THE INVENTION

The present invention provides an automatic external defibrillator (AED) system that combines electrically conductive implantable microelectrodes or microconductors and an adaptor to interface with a separate battery powered electronic device including two or more electrodes configured to operate in conjunction with implanted microelectrodes or microconductors, and at least one capacitor and electrodes to deliver a shock of a predetermined magnitude to the implanted microelectrodes or microconductors.

A conventional smartphone, even under partial charge conditions theoretically has enough stored energy to drive an AED. The present invention is based in part on the realization, in part, that a smartphone battery has enough stored energy to drive an AED, if impedance can be minimized. In one aspect of the invention, an adaptor for a smartphone or the like, has leads including a plurality of needles of the like for pushing into the skin of an individual of cardiac shock. In another aspect, the AED system includes permanently locating microelectrodes or microconductors under the skin of a person at risk.

Several years ago AliveCor introduced a mobile electrocardiogram ("EKG") adapter for smartphones that could be used to diagnose an incidence of cardiac arrest. In the AliveCor mobile EKG adapter, an electrode assembly senses heart-related signals upon contact with a user's skin, and converts the sensed heart-related signals to an EKG electric signal. A converter assembly, integrated with, and electrically connected to the electrode assembly, converts the electric EKG signal generated by the electrode assembly to an ultrasonic frequency modulated EKG sound signal and outputs the ultrasonic frequency modulated sound signal through an audio transmitter at a signal strength capable of being received by a smartphone. Essentially the size of a smartphone and not much thicker than a credit card, the AliveCor mobile EKG adapter allows one to capture EKGs on a smartphone, which can then be relayed to a doctor for analysis and diagnosis.

Defibrillator or cardioversion systems are sometimes provided as implantable cardioverter/defibrillators (ICDs). Such electrodes are typically in the form of patches applied directly to the epicardial tissue, or, through intravascular catheters, are inserted into a selected cardiac chamber. Subcutaneous electrode systems also have been developed.

Subcutaneous defibrillators typically use a pulse monitor/generator surgically implanted into the abdomen and subcutaneous electrodes implanted in the thorax. Subcutaneous defibrillation systems typically use a power source such as an implanted battery and monitoring device implanted in connection with the subcutaneous electrodes. While potentially lifesaving, ICDs require significant invasive surgery.

The present invention provides a method and device that reduces the power requirements of an AED to allow a smartphone or other small electronic device to act as an AED in response to EKG or other data. In accordance with one aspect of the invention, the thoracic impedance of a person is lowered through the use of implanted conductive microconductors or microelectrodes. As used herein "microelectrodes" and "microconductors" are used interchangeably. Currently, microchips are used, for example, to identify pets and children to help locate pets and children in the case of kidnapping or wandering. Essentially, a microchip is injected into the skin of a pet or child. The microchip is coated with an anti-migration coating, so the chip stays permanently in place, and is not rejected by the body. In like manner microelectrodes or microconductors may be implanted in strategic positions on a patient at risk for cardiac arrhythmia, to lower the thoracic impedance of the patient and in turn significantly reduce the power requirements of an AED. The AED may then be powered by a small portable device, such as a smartphone or tablet.

So as to reduce the complexity and length of the Detailed Specification, and to fully establish the state of the art in certain areas of technology, Applicant herein expressly incorporate by reference all of the following materials identified in each numbered paragraph below. The incorporated materials are not necessarily "prior art" and Applicant expressly reserve the right to swear behind any of the incorporated materials.

U.S. Pat. No. 8,615,295
U.S. Pat. No. 8,781,576
U.S. Pat. No. 9,101,778
US Published Application No. 2014/0039593 and
US Published Application No. 2014/0039594
www.alivecor.com
U.S. Pat. No. 8,301,232
U.S. Pat. No. 8,509,882
U.S. Pat. No. 8,700,137
U.S. Pat. No. 9,026,202
U.S. Pat. No. 7,657,311
U.S. Pat. No. 8,050,759
US Published Application No. 2006/0173498
US Published Application No. 2005/0143776
US Published Application No. 2015/0217121
US Published Application No. 2016/0038751

Applicant believes that the material incorporated above is "non-essential" in accordance with 37 CFR 1.57, because it is referred to for purposes of indicating the background of the invention or illustrating the state of the art. However, if the Examiner believes that any of the above-incorporated material constitutes "essential material" within the meaning of 37 CFR 1.57(c)(1)-(3), applicant(s) will amend the specification to expressly recite the essential material that is incorporated by reference as allowed by the applicable rules.

It is an object of the invention to lower the transthoracic impedance of a patient at risk for life-threatening cardiac arrhythmias of ventricular fibrillation and ventricular tachycardia.

It is another object of the invention to provide an AED that is more compact and easily transported.

It is another object of the invention to provide an AED that is more conveniently carried by a user at risk for life-threatening cardiac arrhythmias of ventricular fibrillation and ventricular tachycardia at all times.

It is another object of the invention to provide an AED adapter that may be used in conjunction with a smartphone or tablet.

It is another object of the invention to provide an AED that is less expensive for the end user.

It is another object of the invention to provide an AED that also may receive and collect electrocardiogram data.

It is another object of the invention to provide an AED that will audibly instruct a user or caregiver on how to use the AED.

It is another object of the invention to provide an AED that is simple to use.

SUMMARY OF THE INVENTION

The above and other objects may be achieved using devices involving an automatic external defibrillator (AED) system comprising electrically conductive implantable microelectrodes or microconductors and an adapter to interface with a separate electronic device such as a smartphone or a tablet and the implantable microelectrodes or microconductors. The adapter includes a connector to connect to the device and an electrode configured to operate in conjunction with the implantable microelectrodes or microconductors to significantly lower the transthoracic impedance of the patient. At least one capacitor is provided in the adapter to receive power from the electronic device. When a program or a user or caregiver decides to deliver a shock to the patient's heart, the capacitor(s) are charged and a shock of a predetermined magnitude is delivered to the implantable microelectrodes through the electrodes.

The present invention in one aspect provides among other things an adapter that may be used with a separate electronic device such as a smartphone or tablet as an AED. The adapter operates in conjunction with two or more implantable electrically conductive microelectrodes or microconductors to significantly lower the transthoracic impedance of the patient. When a patient is diagnosed to be at risk for life-threatening cardiac arrhythmias of ventricular fibrillation and ventricular tachycardia, the patient may have two or more of the conductive microelectrodes or microconductors implanted in strategic positions near the patient's heart. The patient may then use the adapter in concert with an electronic device, such as a tablet or smartphone, as a readily transported AED.

The microelectrodes or microconductors are formed of an electrically conductive metal. Preferably the metal comprises a biocompatible metal such as silver or a silver alloy, or a valve metal such as tantalum, titanium or niobium or an alloy thereof. Other metals such as copper or aluminum could be used. However, since the microelectrodes or microconductors are intended for implantation into the body, it is preferable that the microelectrodes or microconductors comprise a biocompatible metal in the event the anti-migration coating is broken. Actually, by forming the microelectrodes or microconductors of biocompatible material, the anti-migration coating may be eliminated.

In one embodiment of the invention, the electrodes of the adapter include a needle pad to penetrate the top layer of the skin and deliver the electric shock directly to the implanted microelectrodes or microconductors. The electrodes of the adapter also may receive signals from the heart, and software in the electronic device may translate the signals received through the electrodes into electrocardiogram data using the AliveCor technology above described. The AED system also may function in connection with a wearable electronic device having its own processor, or with a wearable electronic device coupled with a smartphone or tablet. In some embodiments, the adapter includes its own separate power source, or supplemental power source such as a battery.

In a particular embodiment, the adapter is configured to provide electrocardiogram monitoring of the patient. The electrodes are placed over the implantable microelectrodes or microconductors under the patient's skin and may be held in place by, for example, an adhesive. The adapter includes a power source and a converter assembly, integrated with, and electrically connected to the electrode assembly, to converts the electric EKG signal generated by the electrode assembly to an ultrasonic frequency modulated EKG sound signal. The converter assembly then outputs the ultrasonic frequency modulated sound signal through an audio transmitter at a signal strength capable of being received by the user's smartphone or tablet. When the EKG data allows diagnoses of a life-threatening cardiac arrhythmia of ventricular fibrillation and ventricular tachycardia in the patient, the power source charges the capacitors in the adapter to a predetermined level and delivers an electrical shock which stops the arrhythmia, allowing the heart to reestablish an effective rhythm. Alternatively, the adapter may be connected to the smartphone or tablet and use the power source of the smartphone or tablet to charge the capacitors to deliver the electric shock to the heart.

The above and other objects also may be achieved using methods involving diagnosing and treating cardiac arrhythmias of ventricular fibrillation and ventricular tachycardia in a patient, by providing an EKG/AED adaptor and also providing a software application configured to run the adapter hardware using the processor and associated hardware of the separate electronic device such as a smartphone, tablet or wearable device. The software application may be configured to charge the at least one capacitor to a predetermined level when activated and discharge an electric shock from the at least one capacitor to the implantable microchip through the electrode. In a particular embodiment, the software application may monitor electrocardiogram data received from the adapter and determine when a treatment shock is called for. The software application may provide the treatment shock automatically, or may provide some sort of alarm to alert the patient to the need for a treatment shock. In a particular embodiment, the software application will automatically alert a loved one or emergency services when a treatment shock is delivered to the patient.

Aspects and applications of the invention presented here are described below in the drawings and detailed description of the invention. Unless specifically noted, it is intended that the words and phrases in the specification and the claims be given their plain, ordinary, and accustomed meaning to those of ordinary skill in the applicable arts.

BRIEF DESCRIPTION OF THE DRAWINGS

A more complete understanding of the present invention may be derived by referring to the detailed description when considered in connection with the following illustrative figures. In the figures, like reference numbers refer to like elements or acts throughout the figures.

Figure 1:
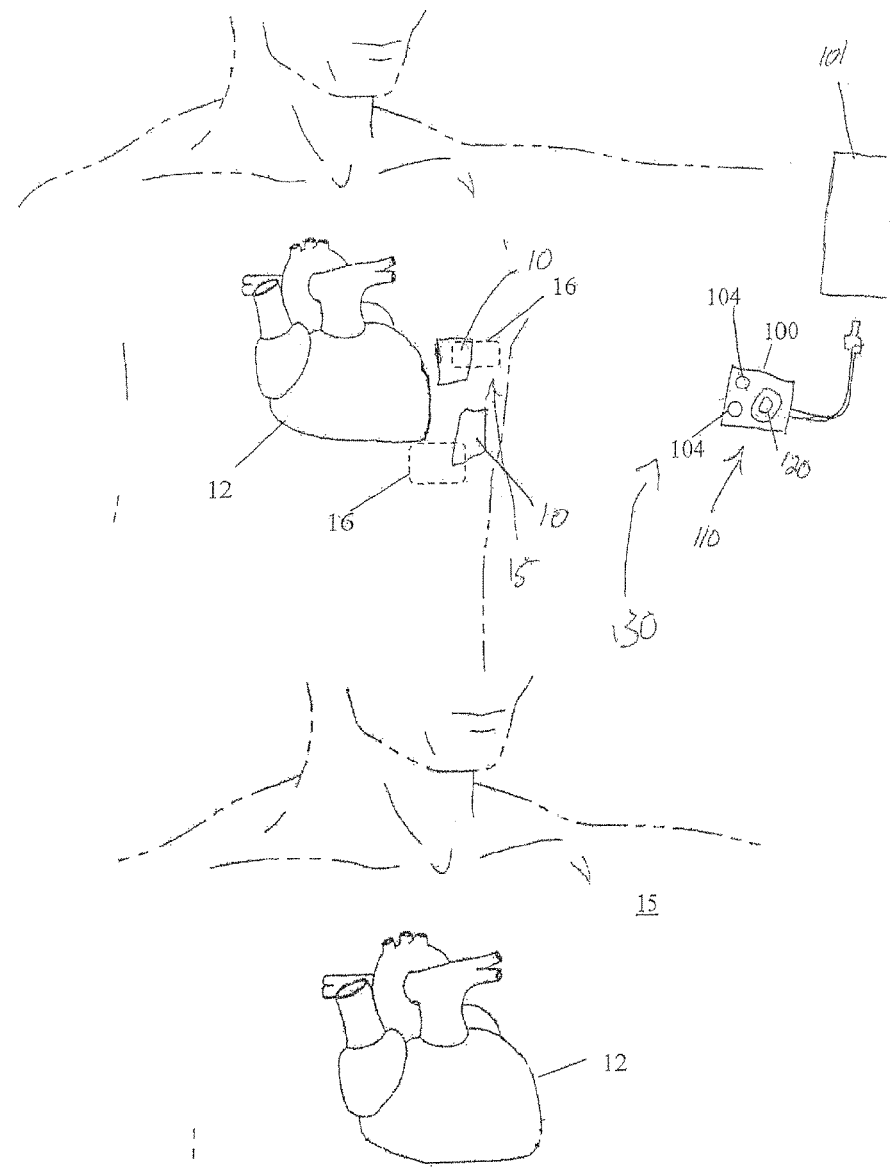
FIG. 1 depicts a schematic view of the implantable microchip implanted in the thorax of a patient and the adapter of the invention.

Elements and acts in the figures are illustrated for simplicity and have not necessarily been rendered according to any particular sequence or embodiment.

DETAILED DESCRIPTION OF THE INVENTION

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention. In many cases, a description of the operation is sufficient to enable one to implement the various forms of the invention, particularly when the operation is to be implemented in software. It should be noted that there are many different and alternative configurations, devices and technologies to which the disclosed inventions may be applied. The full scope of the inventions is not limited to the examples that are described below.

Implantable microelectrodes or microconductors 10 are provided under the skin to significantly lower the thoracic impedance of a person or animal at risk of heart arrhythmia. More specifically, microelectrodes or microconductors 10 containing an electrically conductive metal is placed under the skin 15 of a person or animal deemed to be at risk for cardiac arrest. A person or animal at risk for cardiac arrest may include person or animal with a family history of cardiac problems, or a person or animal who experienced a previous cardiac event. Of course, any person seeking an additional level of preparedness could be provided with micro-conductions.

In one embodiment, a plurality of microelectrodes or microconductors 10 are placed in distinct locations and patterns to optimize current delivery to the heart 12. The microelectrodes or microconductors 10 may be located proximal the left ventricular-cavity 14 on the patient's chest, on the patient's side or back, or any other portion of the body appropriate for providing electrical stimulation to the heart 12. In a preferred embodiment, tattoos shown in phantom at 16 may be placed on the skin 15 of the patient to indicate the location of the implanted microelectrodes or microconductors 10. Tattoos may also be used to alert medical personnel of the presence of the microelectrodes or microconductors 10 so that if the person is subjected to conventional defibrillation, the defibrillator may be adjusted to operate at a reduced charge to avoid possible burns. The tattoos 16 also may include electrically conductive materials to further enhance electrical conductivity of the skin. Alternatively, or additionally, the patient may be provided with a medical bracelet, card or chain carrying an appropriate warning.

Figure 2:
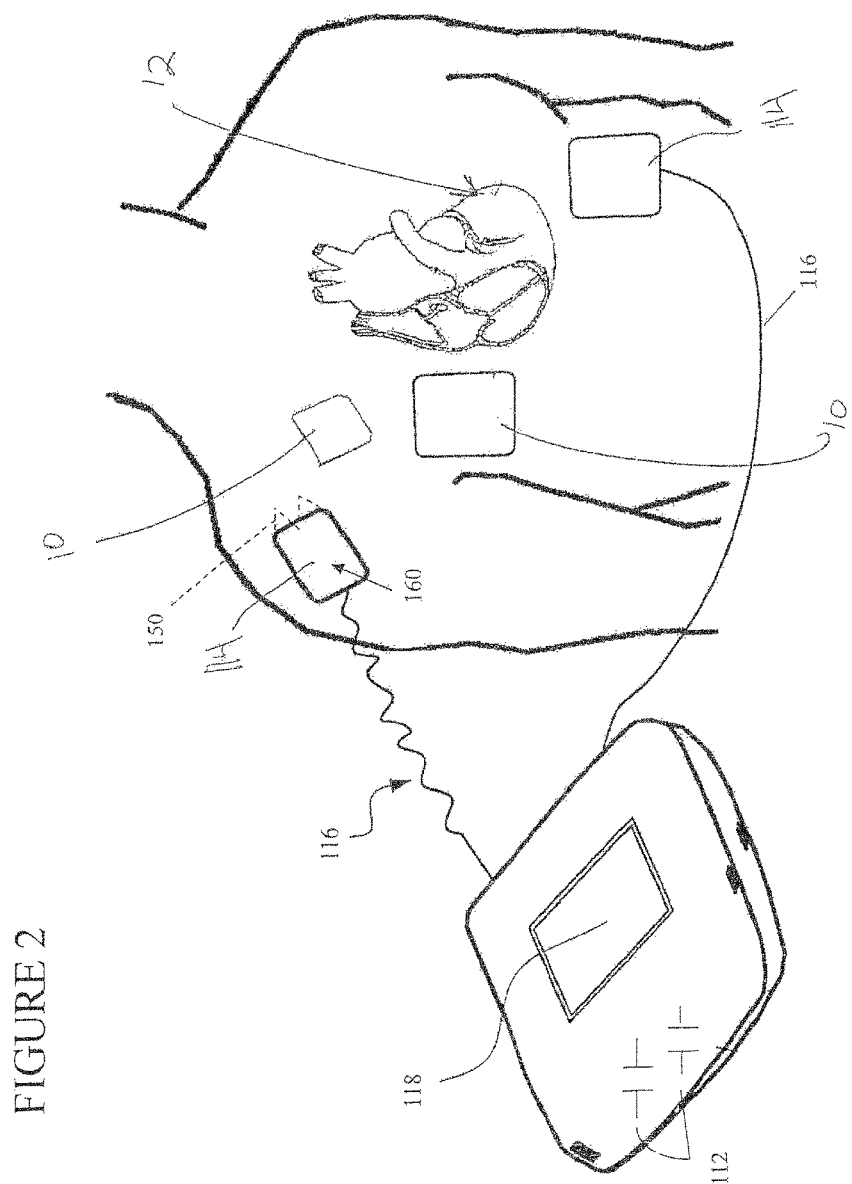
FIG. 2 depicts an alternate schematic view of the implantable microchip implanted in the thorax of a patient and another embodiment of the adapter of the invention.

A smartphone adapter 100 may be provided that allows the user's smartphone or tablet 101 to function as the AED. The smartphone adapter 100 may include an EKG assembly 120 to monitor or diagnose the patient using, e.g., technology similar to that developed by AliveCor. A pair of electrode assemblies 114 are positioned operate in conjunction with the microelectrodes or microconductors 10 or separately to sense heart-related signals upon contact with the patient's skin 15. Electrode assemblies 114 may be similar to conventional AED peel and place electrodes. Alternatively, electrode assemblies 114 may include a plurality of needles, shown in phantom at 150. In the latter case, electrode assemblies 114 may be electrically insulated 160 in part, so as to allow a caretaker to place and hold the electrodes on the person needing treatment. The processor of the smartphone or tablet 101 converts the sensed heart-related signals to an EKG electric signal. In a particular embodiment, a converter assembly integrated with and electrically connected to the electrode assembly converts the electric EKG signal generated by the electrode assembly to an ultrasonic frequency modulated EKG sound signal and outputs the ultrasonic frequency modulated sound signal through an audio transmitter at a signal strength capable of being received by a smartphone 101. In an alternative embodiment, shown in FIG. 2, the EKG signal is sent to a pair of electrode assemblies 114 hard wired 116 through a wired adapter 118 that is plugged directly into the smartphone or tablet 101.

In the event of a cardiac arrhythmia, a shock may be delivered to the patient by the AED. The AED includes an adapter 110 to interface with the smartphone or tablet 101. The adapter 110 includes a connector 111. The connector 111 may be a male firewire interface to interact with, for example, a smartphone or tablets or may be a male microUSB interface or any other connector to interact with a smartphone or tablet 101. The adapter 110 may include one or more capacitors. Power from the smartphone or tablet 101 charges one or more capacitors shown schematically at 112, through the adapter 110. The capacitors are charged to a preprogrammed voltage level by a charging circuit based upon control signals from instructions programmed into an application on the smartphone or tablet 101. A feedback signal allows the smartphone or tablet to determine when the capacitors are charged.

As described above, the adapter 110 includes electrode assemblies 114 that may bridge to the microelectrodes implanted into the patient. In a particular embodiment, the electrode assemblies 114 of the EKG comprise electropads or needle pads 150. In use, a caregiver contacts the electropads or needle pads 150 to the area on the patient's skin 15 under which the microelectrodes 10 are implanted. The capacitors are charged, and then discharged delivering a shock to the patient.

The software for running the adapter 110 could be loaded on the smartphone or tablet 101 or accessed from the Cloud, and may include other automatic features such as GPS and an automatic dialer for automatically calling 911 when the AED is activated. Additionally, the smartphone or tablet's speaker (not shown) may be used to guide the caregiver in the use of the AED. In use, when the AED detects a cardiac event, the smartphone or tablet 101 will execute a program that includes providing instructions over the smartphone or tablet speaker, to the user, on how to use the device to deliver the shock to the patient. Instructions may include instructions on placing the electropads or needle pads 150.

The adapter includes a housing 130 to contain the capacitors, electropads or needle pads 150, connector 110 for the smartphone or tablet, optional batteries, and other necessary hardware, and electrical insulation so that the caregiver neither affects the analysis of the patient's cardiac condition, and also is protected from the shock being administered.

The device should be significantly less costly than conventional stand-alone units, and due to its size may be readily portable and carried on a person.

While the invention has been described as an adaptor for use with a smartphone, the adaptor also may be formed as a standalone unit having the necessary circuits for analyzing the patient's cardiac condition, electrodes, batteries, capacitor and controls for shocking a patient.

I claim:

1. An automatic defibrillator system comprising:
   one or more electrically conductive implantable microelectrodes or microconductors adapted to be subcutaneously implanted in a patient's body;
   ink or a marker adapted to be placed on the patient over a location of the implantable microelectrodes or microconductors: and
   an adapter, configured to interface with a smartphone, a tablet or a wearable device and the implantable microelectrodes or microconductors, wherein the adapter comprises:
      a pair of electrodes configured to operate in conjunction with the implantable microelectrodes or microconductors, and
      a defibrillator circuit including at least one capacitor adapted to receive power from the smartphone, tablet or wearable electronic device and to deliver a shock of a predetermined magnitude to the implantable microelectrodes or microconductors through the pair of electrodes when the pair of electrodes are aligned with the ink or marker.

2. The defibrillator system of claim 1, wherein the electrodes are peel and place electrodes.

3. The defibrillator system of claim 1, wherein the electrodes are needle pads.

4. The defibrillator system of claim 3, wherein the electrodes are electrically insulated, in part.

5. The defibrillator system of claim 1, wherein the adapter further includes an EKG detecting circuit.

6. The defibrillator system of claim 1, wherein the implantable microelectrodes or microconductors are formed of a biocompatible metal.

7. The defibrillator system of claim 6, wherein the microelectrodes or microconductors are formed of silver or a silver alloy.

8. The defibrillator system of claim 7, wherein the microelectrodes or microconductors are coated with an anti-migration coating.

9. The defibrillator system of claim 6, wherein the microelectrodes or microconductors are formed of valve metal selected from the group consisting of tantalum, titanium niobium and an alloy thereof.

10. The defibrillator system of claim 9, wherein the microelectrodes or microconductors are coated with an anti-migration coating.

11. The defibrillator system of claim 6, wherein the microelectrodes or microconductors are coated with an anti-migration coating.

12. The defibrillator system of claim 1, wherein the ink or marker includes electrically conductive material.

13. A method of diagnosing and treating cardiac arrhythmias of ventricular fibrillation and ventricular tachycardia in an animal, wherein the animal has one or more electrically conductive microelectrodes or microconductors subcutaneously implanted in the animal's body and having ink or markers placed on the animal's skin to mark the location of the one or more microelectrodes or microconductors, the method comprising:
   applying a pair of electrodes to the skin of the animal over the ink or markers;

connecting the electrodes to a portable electronic device which includes at least one capacitor, wherein the electronic device further includes non-transitory computer readable media having computer readable program code thereon comprising a series of computer readable program steps;

executing the series of computer readable program steps with the portable electronic device, the computer readable program steps comprising:

detecting electrical signals from the animal's heart;

charging the at least one capacitor to a predetermined level, and discharging an electric shock from the at least one capacitor through the pair of electrodes to the implantable microelectrodes or microconductors when a shockable rhythm is detected from the electrical signals.

14. The method of claim 13, wherein the computer readable program code is further configured to detect the electrical signals from the animal's heart through the electrodes.

\* \* \* \* \*